(12) United States Patent
Tehrani et al.

(10) Patent No.: US 8,412,331 B2
(45) Date of Patent: Apr. 2, 2013

(54) BREATHING THERAPY DEVICE AND METHOD

(75) Inventors: Amir J. Tehrani, Redwood City, CA (US); David Ligon, Redwood City, CA (US)

(73) Assignee: RMX, LLC, San Francisco, CA (US)

( * ) Notice: Subject to any disclaimer, the term of this patent is extended or adjusted under 35 U.S.C. 154(b) by 776 days.

(21) Appl. No.: 10/966,474

(22) Filed: Oct. 15, 2004

(65) Prior Publication Data

US 2005/0085868 A1 Apr. 21, 2005

Related U.S. Application Data

(63) Continuation-in-part of application No. 10/686,891, filed on Oct. 15, 2003.

(51) Int. Cl.
*A61N 1/18* (2006.01)

(52) U.S. Cl. ........................................................ 607/42

(58) Field of Classification Search ...................... 607/42
See application file for complete search history.

(56) References Cited

U.S. PATENT DOCUMENTS

| | | | |
|---|---|---|---|
| 3,773,051 A | 11/1973 | Holcomb et al. | |
| 4,827,935 A | 5/1989 | Geddes | |
| 4,830,008 A | 5/1989 | Meer | 128/421 |
| 5,056,519 A | 10/1991 | Vince | 128/419 |
| 5,146,918 A * | 9/1992 | Kallok et al. | 607/2 |
| 5,174,287 A | 12/1992 | Kallok et al. | 128/419 |
| 5,190,036 A | 3/1993 | Linder | |
| 5,211,173 A | 5/1993 | Kallok et al. | 128/419 |
| 5,215,082 A | 6/1993 | Kallok et al. | 128/419 |
| 5,233,983 A | 8/1993 | Markowitz | 607/42 |
| 5,265,604 A | 11/1993 | Vince | 607/42 |
| 5,281,219 A | 1/1994 | Kallok | 607/42 |
| 5,300,094 A | 4/1994 | Kallok et al. | 607/42 |
| 5,423,327 A | 6/1995 | Clauson et al. | 128/716 |
| 5,483,969 A | 1/1996 | Testerman et al. | |
| 5,485,851 A | 1/1996 | Erickson | 128/716 |
| 5,522,862 A | 6/1996 | Testerman et al. | 607/42 |
| 5,524,632 A | 6/1996 | Stein et al. | 128/733 |
| 5,540,731 A | 7/1996 | Testerman | 607/42 |
| 5,540,732 A | 7/1996 | Testerman et al. | 607/42 |
| 5,540,733 A | 7/1996 | Testerman et al. | 607/42 |

(Continued)

FOREIGN PATENT DOCUMENTS

| | | |
|---|---|---|
| DE | 112004001957 T5 | 8/2006 |
| DE | 112004001953 T5 | 10/2006 |

(Continued)

OTHER PUBLICATIONS

Don D. Sin, Effects of Continuous Positive Airway Pressure on Cardiovascular Outcomes in Heart Failure Patients With and Without Cheyne-Stokes Respiration, *Circulation*, 102:61-66 (Jul. 4. 2000).

(Continued)

*Primary Examiner* — Niketa Patel
*Assistant Examiner* — Alyssa M Alter
(74) *Attorney, Agent, or Firm* — Levine Bagade Han LLP

(57) ABSTRACT

A device and method is provided for electrically stimulating the diaphragm to control breathing while inhibiting respiratory drive. A stimulation phase is identified. The stimulation phase is a period of time within the breathing cycle in which stimulation will inhibit respiratory drive. The respiratory drive inhibition may be used in a number of applications including but not limited to: improving or remodeling the heart in heart failure patients, treating apnea, chronic obstructive pulmonary disorder (COPD), and hypertension.

15 Claims, 8 Drawing Sheets

U.S. PATENT DOCUMENTS

| | | | |
|---|---|---|---|
| 5,546,952 A | 8/1996 | Erickson | |
| 5,549,655 A | 8/1996 | Erickson | |
| 5,572,543 A | 11/1996 | Heinemann et al. | |
| 5,678,535 A | 10/1997 | DiMarco | 128/200.24 |
| 5,766,228 A | 6/1998 | Bonnet et al. | 607/16 |
| 5,797,923 A | 8/1998 | Aiyar et al. | 606/129 |
| 5,800,470 A | 9/1998 | Stein et al. | 607/20 |
| 5,814,086 A * | 9/1998 | Hirschberg et al. | 607/14 |
| 5,830,008 A | 11/1998 | Broschard, III | |
| 5,876,353 A | 3/1999 | Riff | 600/547 |
| 5,895,360 A | 4/1999 | Christopherson et al. | 600/529 |
| 5,911,218 A * | 6/1999 | DiMarco | 128/200.24 |
| 5,944,680 A | 8/1999 | Christopherson et al. | |
| 6,021,352 A | 2/2000 | Christopherson et al. | 607/42 |
| 6,099,479 A | 8/2000 | Christopherson et al. | 600/529 |
| 6,212,435 B1 | 4/2001 | Lattner et al. | 607/134 |
| 6,224,562 B1 | 5/2001 | Lurie et al. | 601/41 |
| 6,251,126 B1 | 6/2001 | Ottenhoff et al. | 607/42 |
| 6,269,269 B1 | 7/2001 | Ottenhoff et al. | 607/42 |
| 6,312,399 B1 | 11/2001 | Lurie et al. | |
| 6,314,324 B1 | 11/2001 | Lattner et al. | |
| 6,345,202 B2 | 2/2002 | Richmond et al. | 607/42 |
| 6,415,183 B1 * | 7/2002 | Scheiner et al. | 607/42 |
| 6,463,327 B1 | 10/2002 | Lurie | |
| 6,480,733 B1 | 11/2002 | Turcott | 600/516 |
| 6,489,447 B1 | 12/2002 | Basey et al. | |
| 6,512,949 B1 | 1/2003 | Combs et al. | |
| 6,527,729 B1 | 3/2003 | Turcott | 600/528 |
| 6,542,774 B2 | 4/2003 | Hill | |
| 6,572,543 B1 | 6/2003 | Christopherson et al. | 600/300 |
| 6,574,507 B1 | 6/2003 | Bonnet | 607/20 |
| 6,587,725 B1 | 7/2003 | Durand et al. | |
| 6,587,726 B2 | 7/2003 | Lurie et al. | |
| 6,589,188 B1 | 7/2003 | Street et al. | 600/538 |
| 6,600,949 B1 | 7/2003 | Turcott | 600/518 |
| 6,633,779 B1 * | 10/2003 | Lee et al. | 607/42 |
| 6,651,652 B1 | 11/2003 | Ward | 128/200.24 |
| 6,731,984 B2 | 5/2004 | Cho et al. | 607/17 |
| 6,735,479 B2 | 5/2004 | Fabian et al. | |
| 6,752,765 B1 | 6/2004 | Jensen et al. | 600/536 |
| 6,770,022 B2 | 8/2004 | Mechlenburg et al. | |
| 6,811,537 B2 | 11/2004 | Bardy | |
| 6,830,548 B2 | 12/2004 | Bonnet et al. | 600/529 |
| 6,881,192 B1 | 4/2005 | Park et al. | |
| 6,908,437 B2 | 6/2005 | Bardy | |
| 7,058,453 B2 | 6/2006 | Nelson et al. | |
| 7,070,568 B1 | 7/2006 | Koh et al. | |
| 7,082,331 B1 | 7/2006 | Park et al. | |
| 7,117,032 B2 | 10/2006 | Childre et al. | |
| 7,277,757 B2 | 10/2007 | Casavant et al. | |
| 7,532,934 B2 | 5/2009 | Lee et al. | |
| 7,610,094 B2 | 10/2009 | Stahmann et al. | |
| 7,840,270 B2 | 11/2010 | Ignagni et al. | |
| 7,970,475 B2 | 6/2011 | Tehrani et al. | |
| 7,979,128 B2 | 7/2011 | Tehrani et al. | |
| 8,116,872 B2 | 2/2012 | Tehrani et al. | |
| 8,140,164 B2 | 3/2012 | Tehrani et al. | |
| 8,255,056 B2 | 8/2012 | Tehrani | |
| 8,280,513 B2 | 10/2012 | Tehrani et al. | |
| 2002/0049482 A1 | 4/2002 | Fabian et al. | |
| 2002/0193697 A1 | 12/2002 | Cho et al. | |
| 2002/0193839 A1 | 12/2002 | Cho et al. | 607/17 |
| 2003/0127091 A1 | 7/2003 | Chang | |
| 2003/0153953 A1 | 8/2003 | Park et al. | 607/17 |
| 2003/0153954 A1 | 8/2003 | Park et al. | 607/17 |
| 2003/0153955 A1 | 8/2003 | Park et al. | 607/17 |
| 2003/0153956 A1 | 8/2003 | Park et al. | 607/17 |
| 2003/0195571 A1 | 10/2003 | Burnes et al. | 607/9 |
| 2003/0204213 A1 | 10/2003 | Jensen et al. | |
| 2003/0225339 A1 | 12/2003 | Orr et al. | |
| 2004/0044377 A1 | 3/2004 | Larsson | |
| 2004/0059240 A1 | 3/2004 | Cho et al. | |
| 2004/0077953 A1 | 4/2004 | Turcott | |
| 2004/0088015 A1 | 5/2004 | Casavant et al. | 607/14 |
| 2004/0111040 A1 | 6/2004 | Ni et al. | 600/534 |
| 2004/0116784 A1 | 6/2004 | Gavish | |
| 2004/0122484 A1 | 6/2004 | Hatlestad et al. | |
| 2004/0134496 A1 | 7/2004 | Cho et al. | 128/204.23 |
| 2004/0138719 A1 | 7/2004 | Cho et al. | 607/42 |
| 2004/0176809 A1 | 9/2004 | Cho et al. | 607/14 |
| 2004/0199221 A1 | 10/2004 | Fabian et al. | |
| 2004/0225226 A1 | 11/2004 | Lehrman et al. | 600/529 |
| 2004/0237963 A1 | 12/2004 | Berthon-Jones | 128/204.26 |
| 2005/0021102 A1 * | 1/2005 | Ignagni et al. | 607/42 |
| 2005/0039745 A1 | 2/2005 | Stahmann et al. | |
| 2005/0043644 A1 | 2/2005 | Stahmann et al. | 600/529 |
| 2005/0043772 A1 * | 2/2005 | Stahmann et al. | 607/42 |
| 2005/0055060 A1 | 3/2005 | Koh et al. | 607/17 |
| 2005/0061315 A1 | 3/2005 | Lee et al. | 128/204.21 |
| 2005/0061319 A1 | 3/2005 | Hartley et al. | 128/204.18 |
| 2005/0061320 A1 | 3/2005 | Lee et al. | 128/204.18 |
| 2005/0065563 A1 | 3/2005 | Scheiner | 607/9 |
| 2005/0065567 A1 | 3/2005 | Lee et al. | 607/17 |
| 2005/0074741 A1 | 4/2005 | Lee et al. | 434/433 |
| 2005/0076909 A1 | 4/2005 | Stahmann et al. | |
| 2005/0080461 A1 | 4/2005 | Stahmann et al. | 607/17 |
| 2005/0085734 A1 | 4/2005 | Tehrani | |
| 2005/0085865 A1 * | 4/2005 | Tehrani | 607/42 |
| 2005/0085866 A1 | 4/2005 | Tehrani | |
| 2005/0085867 A1 | 4/2005 | Tehrani | |
| 2005/0085869 A1 | 4/2005 | Tehrani | |
| 2005/0101833 A1 | 5/2005 | Hsu et al. | 600/26 |
| 2005/0107860 A1 | 5/2005 | Ignagni et al. | 607/116 |
| 2005/0115561 A1 | 6/2005 | Stahmann et al. | 128/200.24 |
| 2005/0119711 A1 | 6/2005 | Cho et al. | |
| 2005/0145246 A1 | 7/2005 | Hartley et al. | 128/203.14 |
| 2005/0148897 A1 | 7/2005 | Cho et al. | 600/533 |
| 2005/0165457 A1 | 7/2005 | Benser et al. | |
| 2005/0240240 A1 | 10/2005 | Park et al. | 607/42 |
| 2005/0261600 A1 | 11/2005 | Aylsworth | |
| 2005/0261747 A1 | 11/2005 | Schuler et al. | |
| 2006/0030894 A1 | 2/2006 | Tehrani | |
| 2006/0036294 A1 | 2/2006 | Tehrani | |
| 2006/0058852 A1 | 3/2006 | Koh et al. | |
| 2006/0064030 A1 | 3/2006 | Cosentino et al. | |
| 2006/0064325 A1 | 3/2006 | Matsumoto et al. | |
| 2006/0122661 A1 | 6/2006 | Mandell | |
| 2006/0122662 A1 | 6/2006 | Tehrani | |
| 2006/0142815 A1 | 6/2006 | Tehrani et al. | |
| 2006/0149334 A1 | 7/2006 | Tehrani et al. | |
| 2006/0155341 A1 | 7/2006 | Tehrani et al. | |
| 2006/0167523 A1 | 7/2006 | Tehrani et al. | |
| 2006/0224076 A1 | 10/2006 | Lange et al. | |
| 2006/0224211 A1 | 10/2006 | Durand et al. | |
| 2006/0247729 A1 | 11/2006 | Tehrani et al. | |
| 2006/0282131 A1 | 12/2006 | Caparso et al. | |
| 2007/0021795 A1 | 1/2007 | Tehrani | |
| 2007/0156199 A1 | 7/2007 | Koh et al. | |
| 2008/0021506 A1 | 1/2008 | Grocela | |
| 2008/0167695 A1 | 7/2008 | Tehrani et al. | |
| 2008/0177347 A1 | 7/2008 | Tehrani et al. | |
| 2008/0183239 A1 | 7/2008 | Tehrani et al. | |
| 2008/0183240 A1 | 7/2008 | Tehrani et al. | |
| 2008/0188903 A1 | 8/2008 | Tehrani et al. | |
| 2008/0188904 A1 | 8/2008 | Tehrani et al. | |
| 2008/0208281 A1 | 8/2008 | Tehrani et al. | |
| 2011/0230932 A1 | 9/2011 | Tehrani et al. | |
| 2012/0158091 A1 | 6/2012 | Tehrani et al. | |

FOREIGN PATENT DOCUMENTS

| | | |
|---|---|---|
| DE | 112004001954 T5 | 10/2006 |
| WO | WO/8600234 | 0/1986 |
| WO | WO 8600234 | 1/1986 |
| WO | WO 2005/037172 | 4/2005 |
| WO | WO 2005/037173 | 4/2005 |
| WO | WO 2005/037174 | 4/2005 |
| WO | WO 2005/037220 | 4/2005 |
| WO | WO 2005/037366 | 4/2005 |
| WO | WO 20051037077 | 4/2005 |
| WO | WO 2007/058938 | 5/2007 |

OTHER PUBLICATIONS

Takaomi Taira, M.D., Ph.D., et. al, Phrenic Nerve Stimulation for Diaphragm Pacing With a Spinal Cord Stimulator *Surg Neurol.* 59:128-132 (2003).

Donald B. Shaul, et. al, Thoracoscopic Placement of Phrenic Nerve Electrodes for Diaphragmatic Pacing in Children *Journal of Pediatric Surgery*, 37:974-978 (Jul. 2002).

Christopher Reeve, New Implantable Breathing Device, *University Hospitals of Cleveland*, pp. 1-4, (2003).

Christopher Reeve, Christopher Reeve Paralysis Foundation Questions & Answers. pp. 1-3 (Mar. 13, 2003).

T. Mitsuyana, et. al, Diaphragm Pacing With the Spinal Cord Stimulator,*Aeta Neurochir*, 87:89-92 (2003).

Harish Aiyar, et. al, Laparoscopic Implant Device for Intermuscular Electrodes, IEEE-EMBC and CMBCC, pp. 1167-1168, ((1995).

Harish Aiyar,et.al, Laparoscopic Implant Instrument for the Placement of Intramuscular Electrodes in the Diaphragm, *Transactions on Rehabilitation Engineering*, pp. 360-371 (Sep. 1999).

Anthony F. DiMarco, et. al, Phrenic Nerve Pacing in a Tetraplegic Patient via lntramuscula Diaphragm Electrodes*American Journal of Respiratory and Critical Care Medicine*. 144: 1604-1606 (2002).

S.Sauermunn, et. al, Computer Aided Adjustment of the Phrenic Pacemaker: Automatic Functions, Documentation, and Quality Control. *Artificial Organs*, 21(3):216-218 (1997).

B.D. Schmit, et. al, An Implantable Impedance Pneumograph Monitor for Detection of Diaphragm Contraction and Airway Obstruction During Diaphragm Pacing, *Medical & Biological Engineering & Computing*, 37:162.168 (1999).

Brian D. Schmit, et. al, Laparoscopic Placement of Electrodes for Diaphragm Pacing Using Stimulation to Locate the Phrenic Nerve Motor Points, *Transactions on Rehabilitation Engineering*, 6(4):382-390 (Dec. 1998).

M. Noshiro, et al., Method of Electrophrenic Respiration for Producing a Natural Respiratory Flow Rate Using Feedback Control of Tidal Volume Waveform, *Med. & Bio. Eng. & Comput.*, 20:763-771, (Nov. 1982).

W. Glenn "Diaphragm Pacing: Present Status" PACE vol. 1 p. 357-370 (1978).

L Bernardi et al "Effect of Rosary Prayer and Yoga Mantras on Autonomic Cardiovascular Rhythms: Comparative Study" BMJ vol. 323 (Dec. 22-29, 2001).

L Bernardi et al "Slow Breathing Increases Arterial Baroreflex sensitivity in Patients with Chronic Heart Failure" Circulation (2002).

A Jensen et al. Signal Transduction in Smooth Muscle: Airway caliber in healthy and asthmatic subjects effects of bronchial challenge and deep inspirations. J. Appl Physiol 91: 506-515 (2001).

Patroniti M.D., et al "Sigh Improves Gas Exchange and Lung Volume in Patients with Acute Respiratory Distress Syndrome Undergoing Pressure Support Ventilation" Anesthesiology 96: 788-94 (2002).

P. Simon et al "Vagal Feedback in the Entrainment of Respiration to Mechanical Ventilation in Sleep ing Humans" J. App. Physiol 89: 760-769 (2000).

R. Gosselink Controlled Breathing and Dyspnea in Patients With Chronic Obstructive Pulmonary Disease. Journal of Rehabilitaiton Research and Development vol. 40, No. 5 , Supplement 2 p. 20-34 (Sep./Oct. 2003).

Shier, D. et al, Hole's Human Anatomy & Physiology,pp. 798 (2 pages total).

Harish, A. et al, "Laparoscopic Implant Device for Intermuscular Electrodes," *IEEE-EMBC and CNBCC*, pp. 1167-1168, 1995.

Series, F. et al, "Increasing the Functional Residual Capacity May Reverse Obstructive Sleep Apnea Sleep," 11(4):349-353, 1988.

U.S. Appl. No. 10/686,891, filed Oct. 15, 2003 in the name of Tehrani, Non-final Office Action mailed Sep. 18, 2009.

U.S. Appl. No. 11/246,439, filed Oct. 11, 2005 in the name of Tehrani, Non-final Office Action mailed Sep. 30, 2009.

U.S. Appl. No. 11/249,718, filed Oct. 13, 2005 in the name of Tehrani, Non final Office Action mailed Apr. 18, 2008.

U.S. Appl. No. 11/249,718, filed Oct. 13, 2005 in the name of Tehrani, Final Office Action mailed Apr. 1, 2009.

U.S. Appl. No. 11/249,718, filed Oct. 13, 2005 in the name of Tehrani, Non-final Office Action mailed Nov. 25, 2009.

U.S. Appl. No. 11/981,800, filed Oct. 31, 2007 in the name of Tehrani et al., Non-final Office Action mailed Oct. 7, 2009.

U.S. Appl. No. 10/966,421, filed Oct. 15, 2004 in the name of Tehrani, Final Office Action mailed Oct. 26, 2009.

U.S. Appl. No. 11/271,554, filed Nov. 10, 2005 in the name of Tehrani et al., Non-final Office Action mailed Dec. 24, 2009.

U.S. Appl. No. 11/981,831, filed Oct. 31, 2007 in the name of Tehrani et al., Non-final Office Action mailed Jan. 6, 2010.

U.S. Appl. No. 10/966,472, filed Oct. 15, 2004 in the name of Tehrani et al., Non-final Office Action mailed Feb. 23, 2010.

U.S. Appl. No. 11/526,949, filed, Sep. 25, 2006 in the name of Tehrani, Final Office Action mailed Mar. 19, 2010.

U.S. Appl. No. 11/271,726, filed Nov. 10, 2005 in the name of Tehrani et al., Non-final Office Action mailed Mar. 31, 2010.

U.S. Appl. No. 11/271,264, filed Nov. 10, 2005 in the name of Tehrani et al., Non-final Office Action mailed Mar. 30, 2010.

U.S. Appl. No. 11/271,315, filed Nov. 10, 2005 in the name of Tehrani et al., Final Office Action mailed Mar. 31, 2010.

U.S. Appl. No. 11/271,315, filed Nov. 10, 2005 in the name of Tehrani et al., Non-final Office Action mailed Oct. 3, 2008.

U.S. Appl. No. 11/981,342, filed Oct. 31, 2007 in the name of Tehrani et al., Non-final Office Action mailed Apr. 15, 2010.

U.S. Appl. No. 11/480,074, filed Jun. 29, 2006 in the name of Tehrani et al., Final Office Action mailed Apr. 30, 2010.

U.S. Appl. No. 10/966,421, filed Oct. 15, 2004 in the name of Tehrani, non-final Office Action mailed Jun. 9, 2010.

U.S. Appl. No. 12/080,133, filed Apr. 1, 2008 in the name of Tehrani et al., non-final Office Action mailed Jun. 10, 2010.

U.S. Appl. No. 11/246,439, filed Oct. 11, 2005 in the name of Tehrani, final Office Action mailed Jun. 29, 2010.

Iazzo, P. ed., "Handbook of Cardiac Anatomy, Physiology, and Devices", p. 398, 2009.

Liem, L.B., "EP 101: Ventricular Tachycardia", EP Lab Digest, vol. 7, No. 8, Aug. 2007.

Malkin R. et al., "The Effect of Inducing Ventricular Fibrillation with 50-Hz Pacing Versus T are Stimulation on the Ability to Defibrillate", Pacing and Clinical Electrophysiology, vol. 21, issue 5, May 1998.

U.S. Appl. No. 11/249,718, filed Oct. 13, 2005 in the name of Tehrani, final Office Action mailed Sep. 14, 2010.

U.S. Appl. No. 10/686,891, filed Oct. 15, 2003 in the name of Tehrani, final Office Action mailed Sep. 15, 2010.

U.S. Appl. No. 11/526,949, filed Sep. 25, 2006 in the name of Tehrani, non-final Office Action mailed Oct. 5, 2010.

U.S. Appl. No. 11/981,342, filed Oct. 31, 2007 in the name of Tehrani et al., final Office Action mailed Oct. 7, 2010.

U.S. Appl. No. 11/271,554, filed Nov. 10, 2005 in the name of Tehrani et al., final Office Action mailed Jan. 31, 2011.

U.S. Appl. No. 11/981,800, filed Oct. 31, 2007 in the name of Tehrani et al., final Office Action mailed Jan. 20, 2011.

U.S. Appl. No. 10/966,421, filed Apr. 8, 2008 in the name of Tehrani, final Office Action mailed Feb. 17, 2011.

U S. Appl. No. 10/686,891, filed Oct. 15, 2003 in the name of Tehrani , non-final Office Action mailed Mar. 30, 2011.

U.S. Appl. No. 11/981,727, filed Oct. 31, 2007 in the name of Tehrani et al., non-final Office Action mailed Apr. 4, 2011.

U.S. Appl. No. 11/480,074, filed Jun. 29, 2006 in the name of Tehrani et al., non-final Office Action mailed Mar. 16, 2011.

U.S. Appl. No. 11/249,718, filed Oct. 13, 2005 in the name of Tehrani, non-final Office Action mailed Apr. 1, 2011.

U.S. Appl. No. 11/271,726 filed Nov. 10, 2005 in the name of Tehrani et al., non-final Office Action mailed Apr. 4, 2011.

U.S. Appl. No. 11/271,264 filed Nov. 10, 2005 in the name of Tehrani et al., final Office Action mailed Apr. 7, 2011.

Heinzer, R., et al, "Lung volume and Continuous Positive Airway Pressure Requirements in Obstructive Sleep Apeau" *American Journal of Respiratory and Critical Care Medicine*, vol. 172, pp. 114-117, 2005.

DiMarco, A F., "Combined Intercostal and Diaphragm Pacing to Provide Artificial Ventilation in Patients With Tetraplegia" *Arch Phys Med Rehabil*, vol. (86), pp. 1200-1207, 2005.

Dunn, R., "Diaphragm and Accessory Respiratory Muscle Stimulation Using Intramuscular Electrodes" *Arch Phys Med Rehabil*, vol. (76), pp. 266-271, 1995.

Glenn, W., et al. "Diaphragm Pacing" *Journal of Thoracic and Cardiovascular Surgery*, vol. (75):2, pp. 273-281, 1978.

U.S. Appl. No. 11/271,726, filed Nov. 10, 2005 in the name of Tehrani et al., Notice of Allowance mailed May 18, 2011.

U.S. Appl. No. 11/271,264, filed Nov. 10, 2005 in the name of Tehrani et al., Notice of Allowance mailed May 20, 2011.

"Quadripolar Pacing Addresses Issues Without Moving Leads," *Diagnostic & Invasive Cardiology*, 1 page, Jun. 1, 2010, Scranton Gillette Communications.

Abraham, W., "Advances in Heart Failure Therapy in the Primary Care Context," *Medscape Family Medicine/Primary Care*, 7 pages, 2004.

Arzt, M. et al, "Treatment of Sleep Apnea in Heart Failure," *AJRCCM*, 36 pages, Mar. 9, 2006.

Boston Scientific, "Diaphragm Stimulation During Daily LV Lead Impedance Measurements", Product Education Brochure, 2 pages, Sep. 26, 2008.

Bradley, T.Q. et al, "Sleep Apnea and Heart Failure, Part I: Obstructive Sleep Apnea," *Circulation*, pp. 1671-1678, Apr. 1, 2003.

Fessler, H.E., "Heart-Lung Interactions: Applications in the Critically Ill," *Eur. Respir. J.*, vol. 10, pp. 226-237, 1997.

Fichter, J. et al, "Sleep-Related Breathing Disorders are Associate with Ventricular Arrhythmias in Patients with an Implantable Cardioverter-Defibrillator," *Chest*, vol. 122, pp. 558-561, Aug. 2002.

Garrigue, S. et al "Sleep Apnea: A New Indication for Cardiac Pacing?," *Pace*, vol. 27, pp. 204-211, Feb. 2004.

Hayano, J. et al "Respiratory Sinus Arrhythmia: A Phenomenon Improving Pulmonary Gas Exchange and Circulatory Efficiency," *Circulation*, vol. 94, pp. 842-847, 1996.

Hennersdorf, M.G. et al, "Chemoreflexsensitivity in Chronic Heart Failure Patients," *European Journal of Heart Failure*, vol. 3, pp. 679-684, 2001.

Ishii, K. et al "Effects of Bilateral Transvenous Diaphragm Pacing on Hemodynamic Function in Patents after Cardiac Operations," *J Thorac Cardiovasc Surg*, vol. 100, pp. 108-114, 1990.

Javaheri, S. et al, "Sleep Apnea in 81 Ambulatory Male Patients with Stable Heart Failure: Types and Their Prevalences, Consequences, and Presentations," *Circulation*, vol. 97, pp. 2154-2159, 1998.

Kohnlein, T. et al, "Central Sleep Apnea Syndrome in Patients with Chronic Heart Disease: a Critical Review of the Current Literature," *Thorax*, vol. 57, pp. 547-554, 2002.

Krachman, S. et al "Comparison of Oxygen Therapy with Nasal Continuous Positive Airway Pressure on Cheyne-Stokes Respiration During Sleep in Congestive Heart Failure," *Chest*, vol. 116, pp. 1550-1557, Dec. 1999.

LaFond, C. et al "Impact of CPAP on Asthmatic Patients with Obstructive Sleep Apnoea," *Eur Respir J*, vol. 29, pp. 307-311, 2007.

Lanfranchi, P.A. et al, "Prognostic Value of Nocturnal Cheyne-Stokes Respiration in Chronic Heart Failure," *Circulation*, pp. 1435-1440, 1999.

Leung, R. et al, "Sleep Apnea and Cardiovascular Disease," *Am J Respir Crit Care Med.* vol. 164, pp. 2147-2165, 2001.

Mathew, O., "Effects of Transient Intrathoracic Pressure Changes (hiccups) on Systemic Arterial Pressure," *J Appl Physiol*, vol. 83, pp. 371-375, 1997.

Norton, J., "Toward Consistent Definitions for Preload and Afterload," *Advan in Physiol Edu.* vol. 25, pp. 53-61, Mar. 2001.

Peters, J. et al, "Negative Intrathoracic Pressue Decreases Independently Left Ventricular Filling and Emptying," *American Physiological Society*, pp. H120-H131, 1989.

Pinsky, M. "Cardiovascular Issues in Respiratory Care," *Chest*, vol. 128, pp. 592-597, Nov. 2005.

Schultz, R. et al "Nocturnal Periodic Breathing in Primary Pulmonary Hypertension," *Eur Respir J*, vol. 19, pp. 658-663, 2002.

Series, F. et al, "Assessment of Upper Airway Stabilizing Forces with the Use of Phrenic Nerve Stimulation in Conscious Humans," *J App Physiol*, vol. 94, pp. 2289-2295, 2003.

Sorli, J. et al., "Ventilatory Assist Using Electrical Stimulation of AJdominal Muscles," *IEEE Transactions of Rehabilitation Engineering*, vol. 4, No. 1, pp. 1-6, Mar. 1996.

Van Houwelingen, K. et al "The Sleep Apnoea Syndromes," *European Heart Journal*, vol. 20, pp. 858-866, Jun. 1999.

Viasys Healthcare, "Ventilation Requires Perfect Balance", SensorMedics® 3100A HFOV, VIASYS Healthcare Brochure, 2 pages.

Wolk, R. et al "Sleep-Disordered Breathing and Cardiovascular Disease," *Circulation*, vol. 108, pp. 9-12, Jul. 2003.

Yim, S. et al "Continuous Positive Airway Pressure for Asthma: Not a Big Stretch?," *Eur Respir J*, vol. 29, pp. 226-228, 2007.

\* cited by examiner

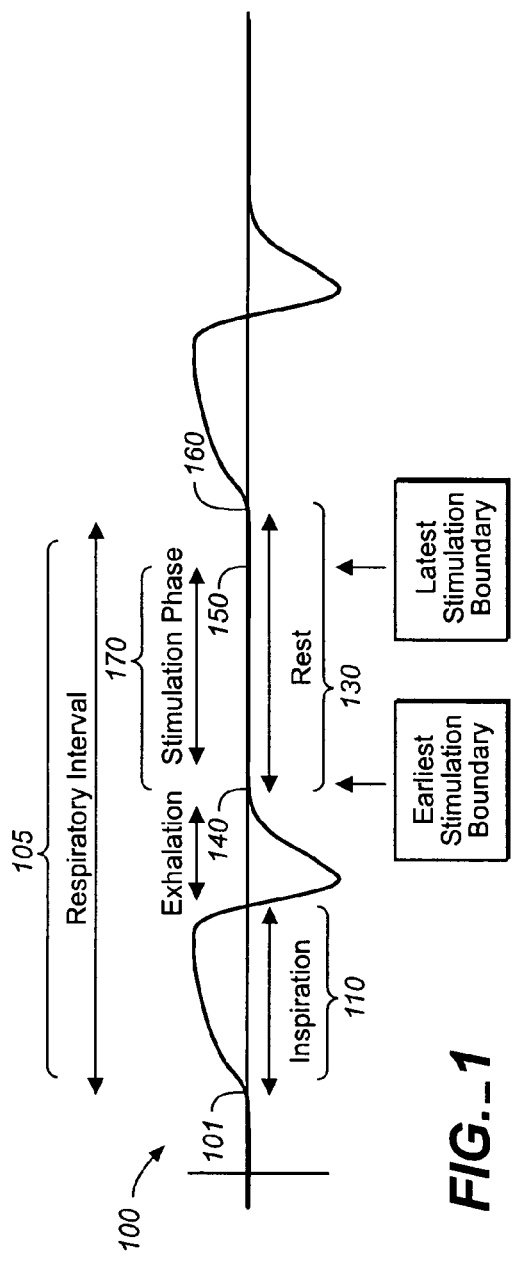
FIG._1
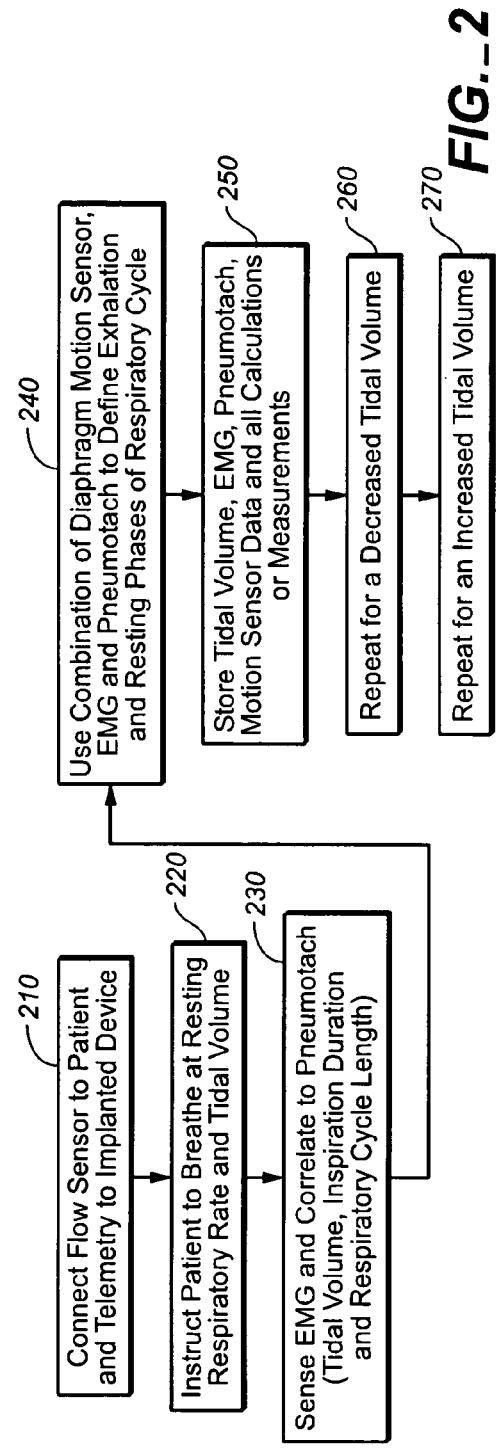
FIG._2

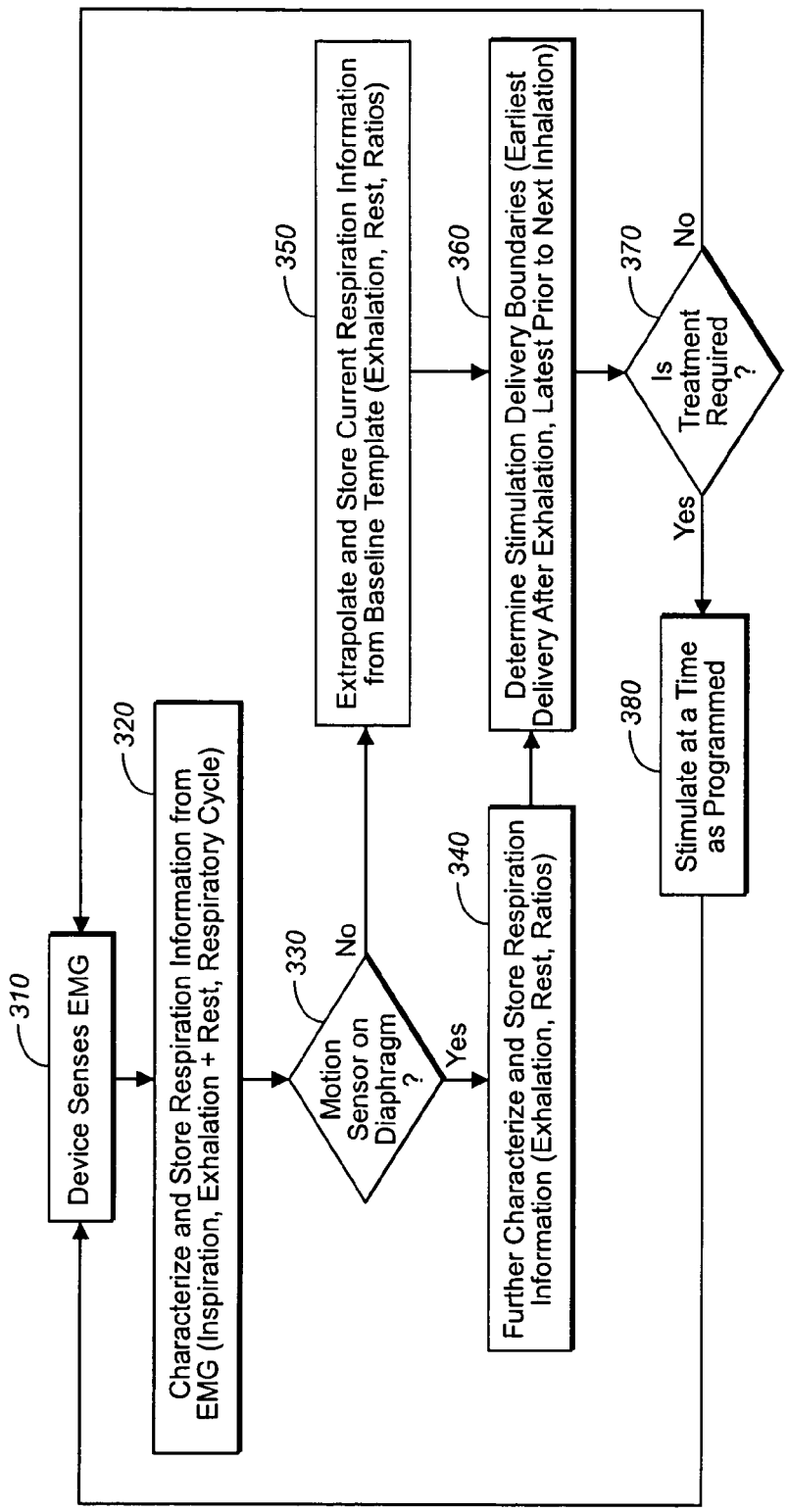
FIG._3

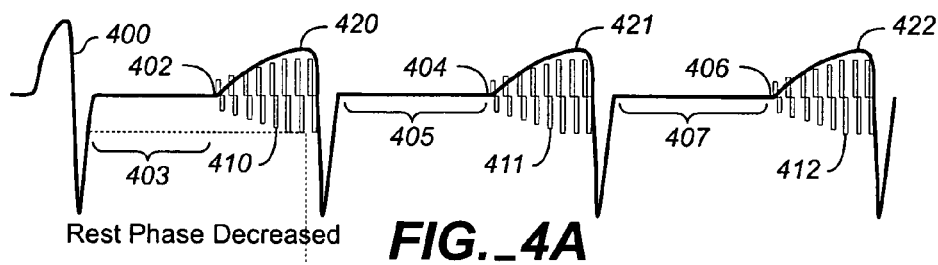
Rest Phase Decreased    FIG._4A
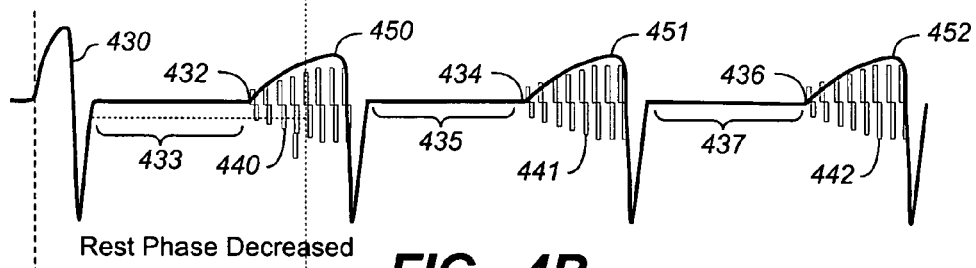
Rest Phase Decreased    FIG._4B
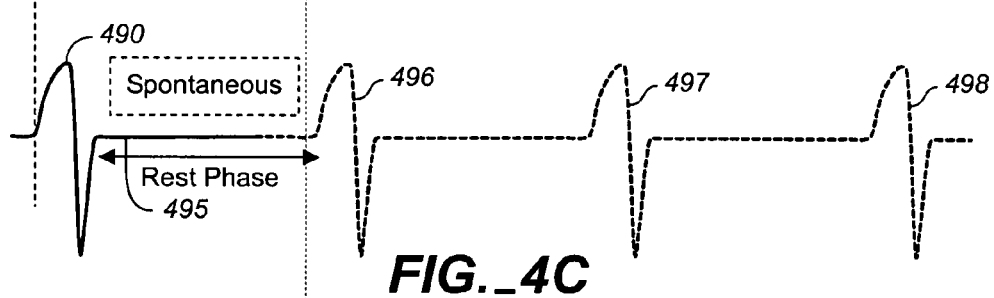
FIG._4C
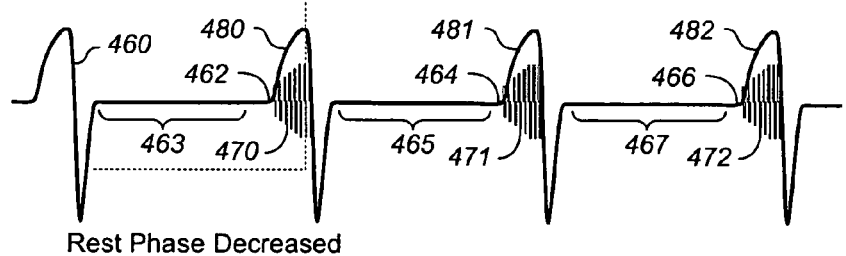
Rest Phase Decreased
FIG._4D

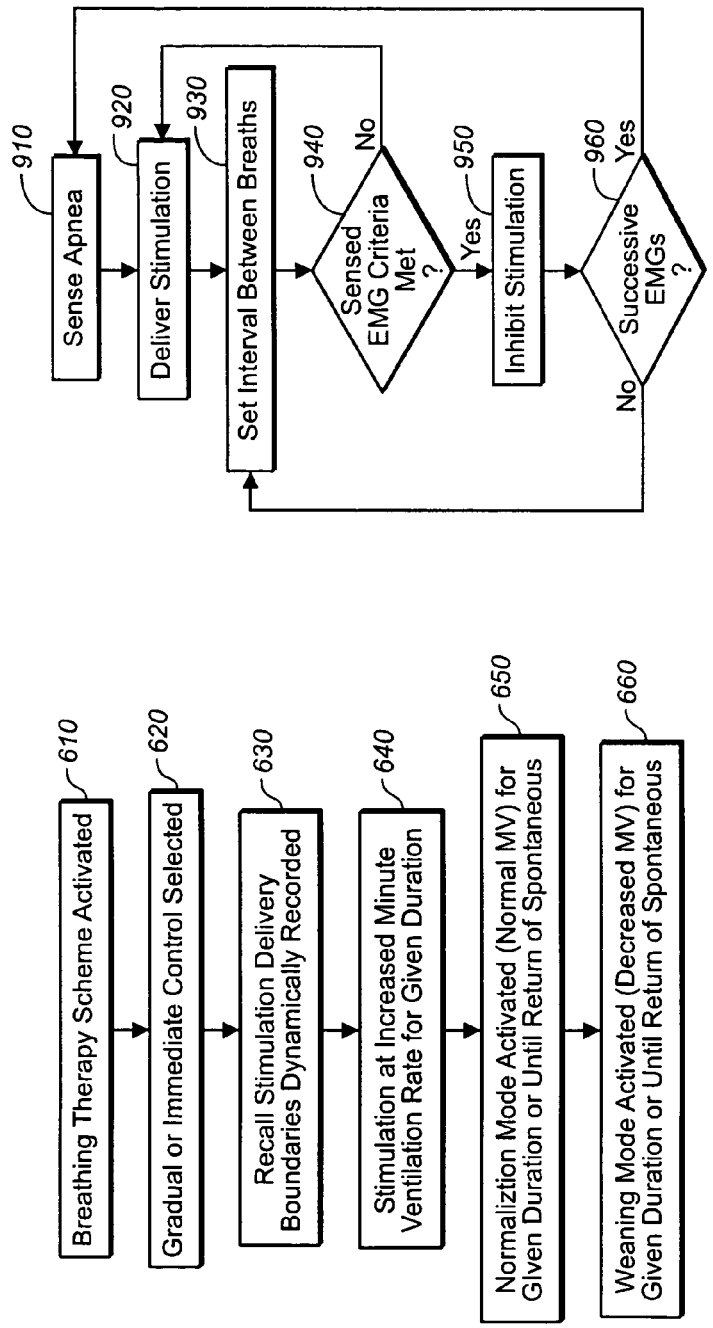

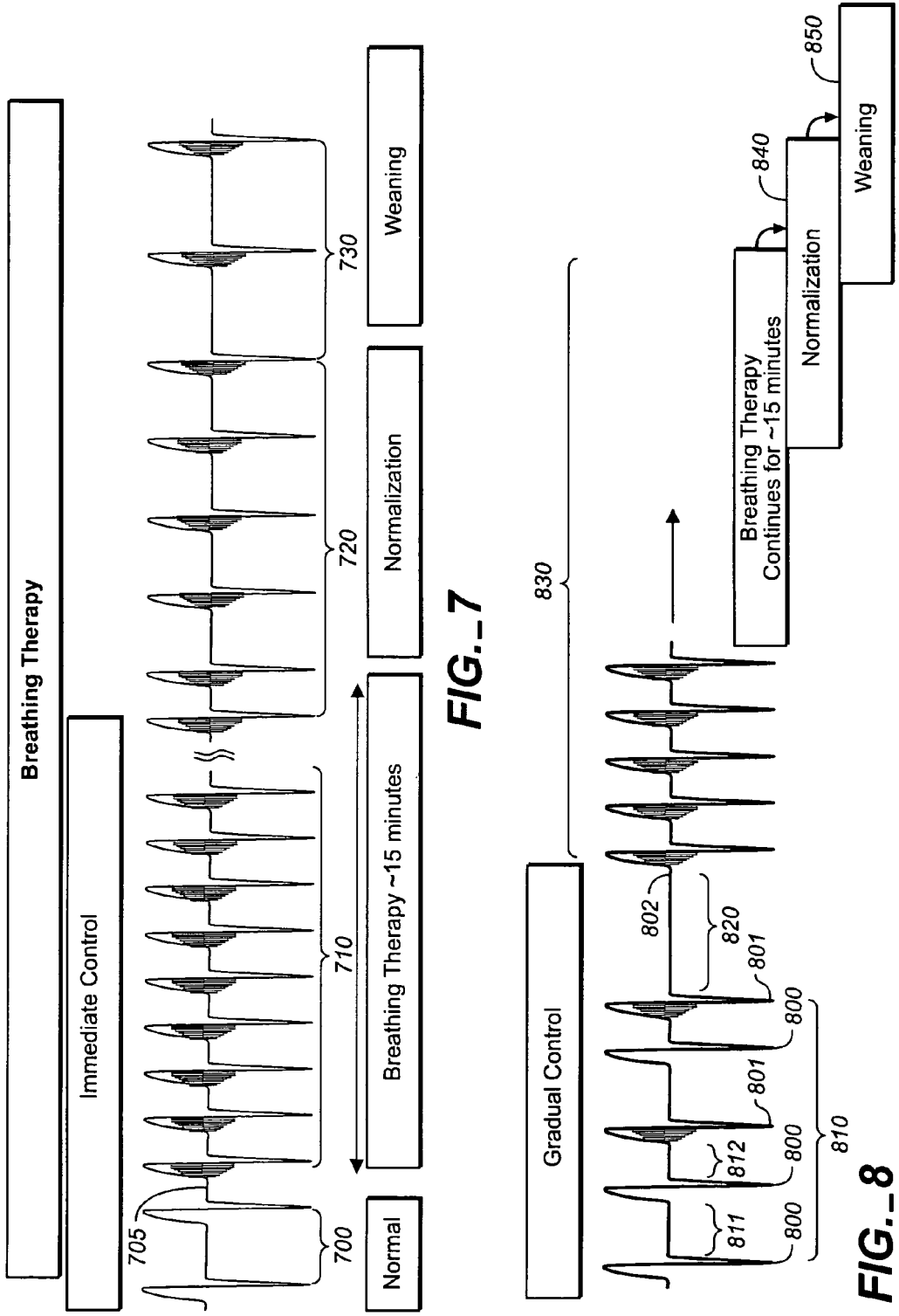

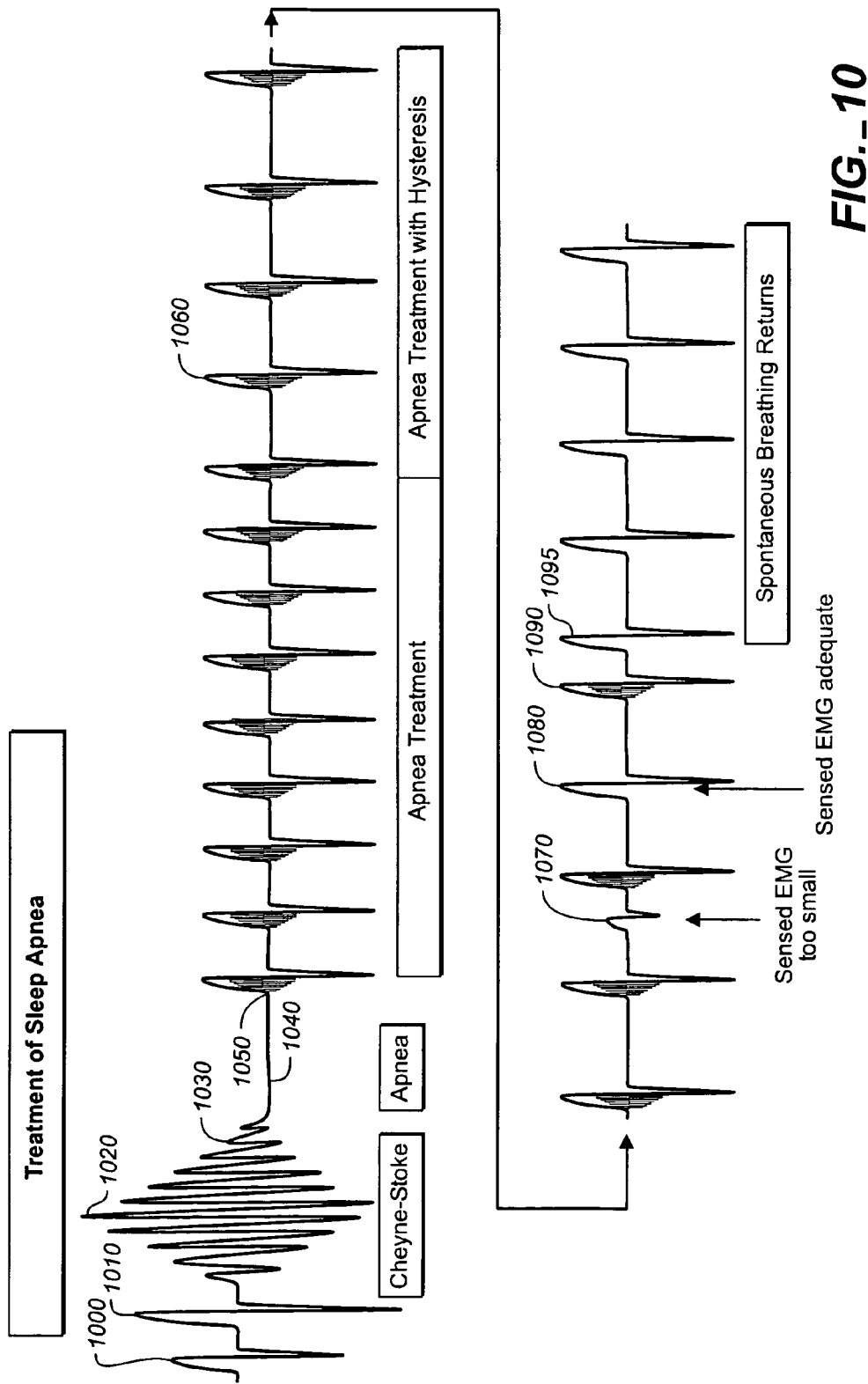
FIG._10

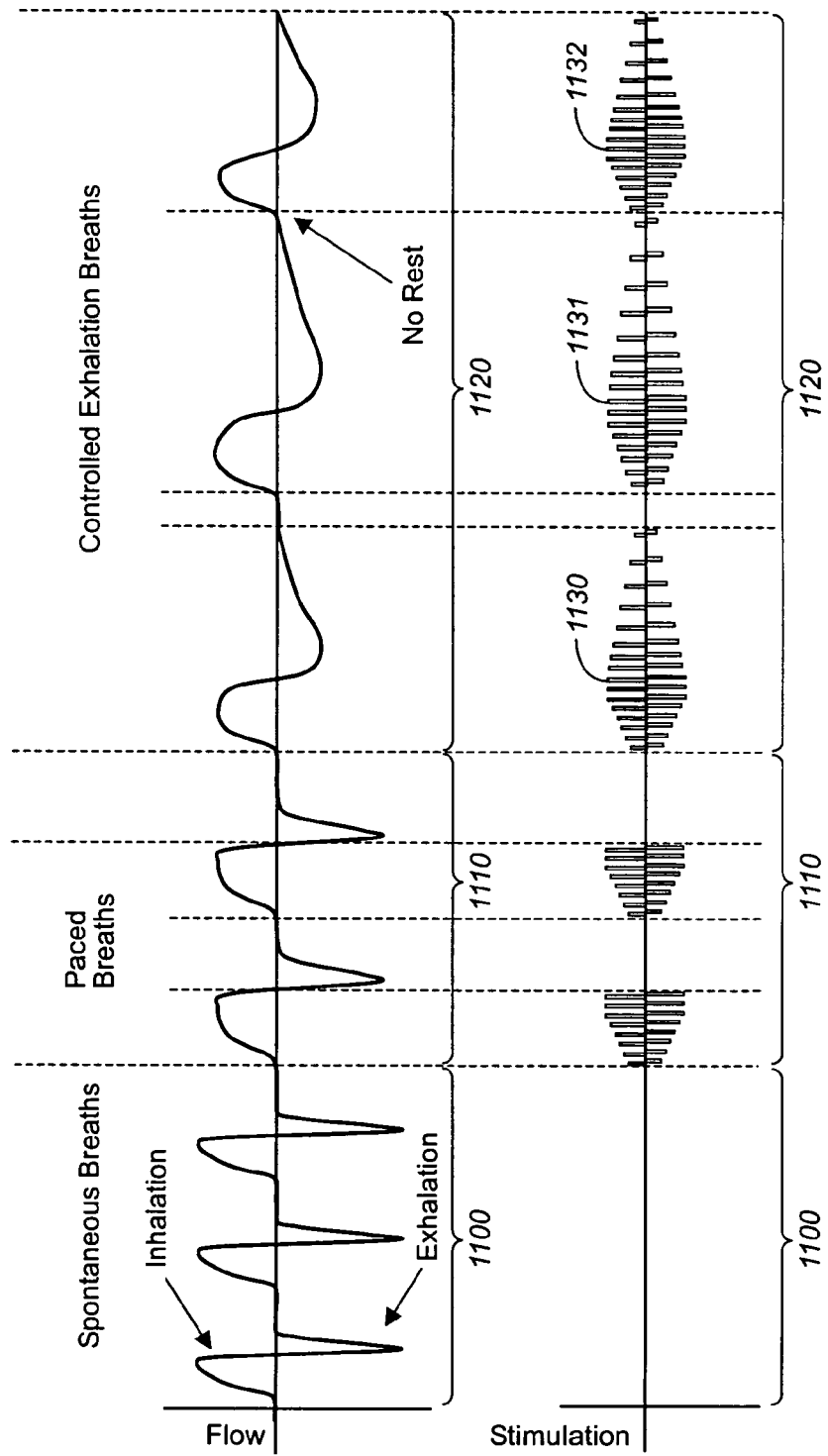
FIG._11

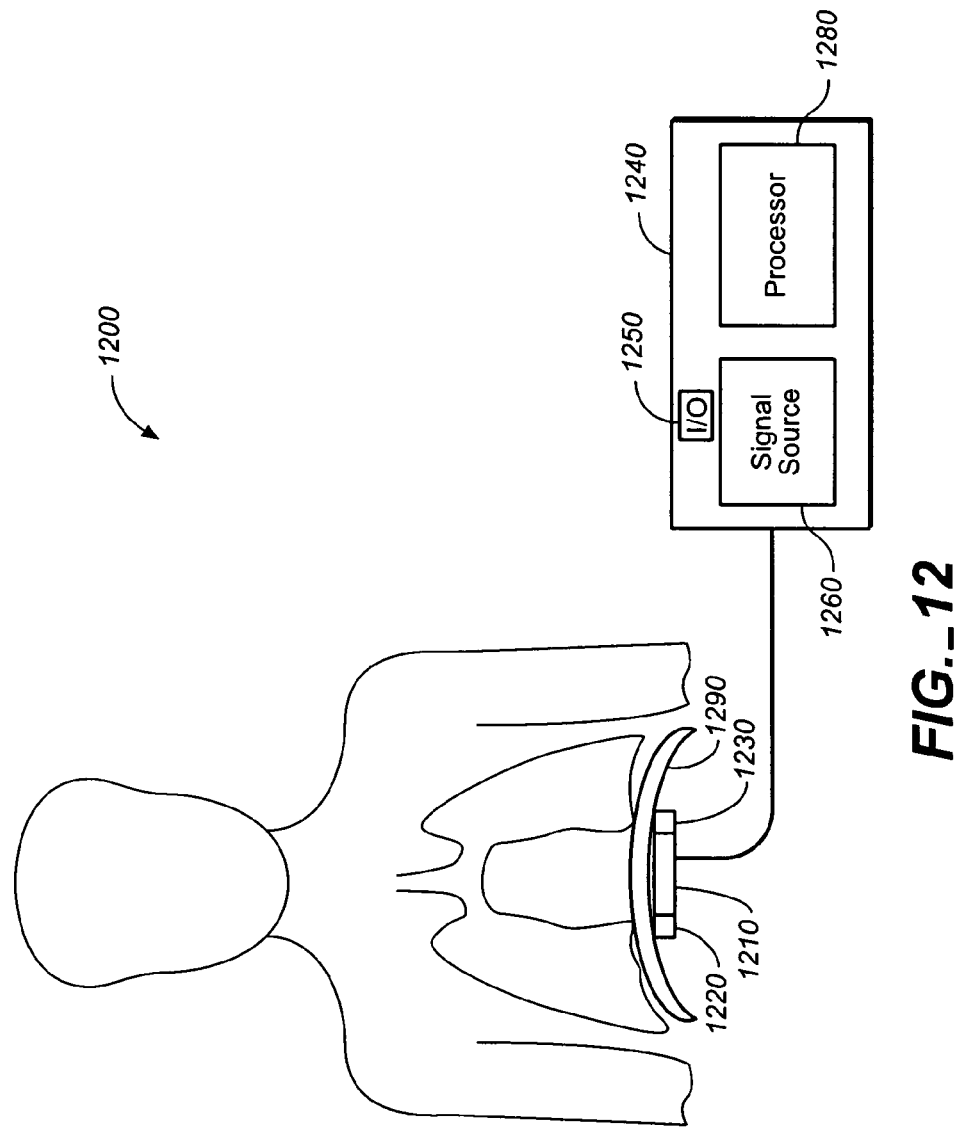
FIG._12

BREATHING THERAPY DEVICE AND METHOD

RELATED APPLICATION DATA

This application is a continuation-in-part of U.S. application Ser. No. 10/686,891 filed Oct. 15, 2003, fully incorporated herein by reference.

FIELD OF THE INVENTION

The invention relates to a device and method for detection, diagnosis and treatment of breathing disorders and to the management of pulmonary or cardiac rhythms, heart failure and other cardiac and/or respiratory related conditions.

BACKGROUND OF THE INVENTION

Diaphragm stimulation has been used to provide breathing in patients unable to breath on their own. Diaphragm stimulation has also been proposed to treat sleep apnea. However, these uses of diaphragm stimulation have not provided optimal breathing responses or control of breathing.

Accordingly it would be desirable to provide improved diaphragm stimulation.

Breathing is typically intrinsically controlled by complex brain control and feedback sensing by the body. The body's involuntary control of respiration is mediated by the brain's respiratory center located in the brainstem, particularly in the medulla oblongata and pons. The respiratory center regulates the rhythmic alternating cycles of inspiration and expiration. The dorsal respiratory group within the medulla is responsible for the generation of respiratory rhythm through a reciprocal inhibition with other cell groups.

In addition, various central and peripheral receptors, e.g., chemoreceptors and mechanoreceptors play important roles in regulation of inspiration.

Central chemoreceptors of the central nervous system located on the ventrolateral medullary surface, are sensitive to pH of their environment. It is believed that these chemoreceptors act to detect a change in pH of the cerebral spinal fluid. An increase in carbon dioxide tension of the arteries will indirectly cause the blood to become more acidic; the cerebral spinal fluid pH is closely comparable to plasma pH, as carbon dioxide easily diffuses across the blood/brain barrier. The detection of variation in the arterial carbon dioxide tension acts as a quick response system, useful in short term regulation. This system utilizes a negative feedback system, therefore if the pH of the cerebral spinal fluid is too low, then the receptor is believed in effect send an error signal to the medulla and respiration is adjusted accordingly.

Peripheral chemoreceptors are believed most importantly to act to detect variation of the oxygen in the arterial blood, in addition to detecting arterial carbon dioxide and pH. These receptors are typically referred to as aortic or carotid bodies, and respectively are location on the arch of the aorta and on the arch of the common carotid artery. A continuous signal is sent, via cranial nerves from the peripheral chemoreceptors. With a decrease in arterial oxygen tension, the signal intensifies, calling for an increase in respiration. However, increase in respiration typically results in falling PCO2 and hydrogen ion concentration which creates strong respiratory inhibitory effects that oppose the excitatory effects of diminished oxygen.

Mechanoreceptors are located for example, in the airways and parenchyma, and are responsible for a variety of reflex responses.

Pulmonary Stretch Receptors are located in smooth muscles of the trachea down to the terminal bronchioles. They are innervated by large, myelinated fibers and they discharge in response to distension of the lung. Their vagally mediated inhibition of inspiration and promotion of expiration is believed to be sustained as long as the lung is distended. They contribute to what is known as the Hering-Breuer reflex which prevents over-inflation of the lungs, by providing feedback signals that cause termination of inspiration.

Other receptors, such as respiratory proprioreceptors located in muscle spindle endings and tendon organs of the respiratory muscles, are stimulated in response to rib movement or intercostals/diaphragmatic tendon force of contraction.

In addition to involuntary control of respiration by the respiratory center, respiration can be affected by conditions such as, e.g., emotional state via input from the limbic system, or temperature, via the hypothalamus. Voluntary control of the respiration is provided via the cerebral cortex, although chemoreceptor reflex is capable of overriding conscious control.

Known diaphragm stimulation techniques have not interacted with this complex respiratory control system to override, influence or work with the system.

Accordingly improved stimulation devices and methods would be desirable.

SUMMARY OF THE INVENTION

The invention provides a device and method for electrically stimulating the diaphragm to control breathing while inhibiting respiratory drive. According to the invention, a stimulation phase is identified. The stimulation phase is a period of time within the breathing cycle in which stimulation will inhibit respiratory drive and most likely will occur during a first fraction of the rest phase. Baseline breathing is sensed and stored. The length of the rest period in a breathing cycle is identified and a stimulation phase is determined.

The baseline is used to determine when to stimulate. The stimulator may include a pulse generator configured to deliver stimulating pulses. EMG or other respiratory indicators may be sensed on a breath by breath basis or over time to determine when to stimulate within the respiratory phase. For a given tidal volume stimulation amplitude, duration and respiratory rate may be varied to inhibit respiratory drive when stimulating.

The respiratory drive inhibition may be used in a number of applications such as improving or remodeling the heart in heart failure patients, treating apnea, chronic obstructive pulmonary disorder (COPD), and hypertension.

DESCRIPTION OF THE DRAWINGS

FIG. 1 is an exemplary respiratory waveform with an identified stimulation phase in accordance with the invention.

FIG. 2 is a flow showing a baseline establishment in accordance with the invention.

FIG. 3 is a flow chart showing identification of delivery boundaries in accordance with the invention.

FIGS. 4A-4D illustrate various stimulation schemes in accordance with the invention, for controlling breathing in comparison to intrinsic breathing.

FIG. 5 is a table illustrating a breathing therapy scheme in accordance with the invention.

FIG. 6 is a flow chart showing a breathing therapy scheme in accordance with the invention.

FIG. 7 illustrates an immediate control mode of a breathing therapy device in accordance with the invention.

FIG. 8 illustrates a gradual control scheme in accordance with the invention.

FIG. 9 is a flow chart showing an apnea control in accordance with the invention.

FIG. 10 illustrates treatment of apnea in accordance with the invention.

FIG. 11 illustrates a breathing therapy mode in accordance with the invention.

FIG. 12 illustrates a diaphragm stimulator in accordance with the invention.

DETAILED DESCRIPTION

In accordance with the invention a diaphragm stimulation device as shown in FIG. 12 is used. The diaphragm stimulation device 1200 electrically stimulates the diaphragm 1290 with an electrical signal supplied from a signal source 1260 to at least one electrode 1220 on an implantable unit 1210. The electrode may also sense EMG of the diaphragm which may include respiration parameters. The sensed EMG is communicated to a processor 1280 of a control unit 1240. The control unit also includes an input/output device 1250 for coupling to external communications device. The input/output device 1250 may be used to communicate to or from the device 1210 or the processor 1280 to or from a programmer, user or provider (e.g. via telemetry, wireless communications or other user/provider/programmer interface). The implantable unit 1210 also includes a motion sensor 1230 that senses the motion of the diaphragm 1290 to determine respiration parameters or responses to stimulation. The motion sensor 1230 may also be used to sense patient activity levels. The sensed signals are communicated to a processor 1280 that stores and uses the motion and EMG signals, as described herein, to control breathing. In addition to stimulation of the diaphragm the phrenic nerve may be stimulated to control breathing.

Referring to FIG. 1 an intrinsic breathing waveform 100 is illustrated. The waveform 100 has a total respiratory interval length 105 that comprises an inspiration period 110, followed by an exhalation period 120 and ending in a rest period 130. The respiratory interval 105 begins at the beginning 101 of the inspiration period 110 and ends at the end 160 of the rest period 130 which is the beginning of the next respiratory cycle. In accordance with the invention as described below a time period is identified for stimulating a diaphragm and/or phrenic nerve to elicit a breathing response where the stimulation is believed to capture or take over breathing control and/or inhibit breathing driven by a subject's innate respiratory drive. The stimulation period 170 is identified by an earliest acceptable stimulation boundary 140 and a latest acceptable stimulation boundary 150.

In general the stimulation period 170 falls within the rest period 130. The earliest stimulation boundary 140 may be selected on a patient by patient basis and is the earliest time at which the innate respiratory drive is captured by a particular stimulation. The stimulation boundary may be determined, e.g., on a patient by patient basis by optimizing stimulation response prior to implanting the device. Accordingly stimulation is provided and observed at different times near the beginning of the rest period to identify when the respiratory drive is captured for a particular stimulation waveform. In general, it is believed that such earliest stimulation boundary 140 is after the end of the exhalation period 120 and at or near the beginning of the rest cycle 130. As an alternative to optimizing on a patient by patient basis an earliest time may be selected for example as the end of the exhalation period 120 or a given time after the end of the exhalation cycle. It may also be selected as a predetermined fraction of the respiratory interval or its various components based on a baseline respiratory interval or interval component.

The latest stimulation boundary 150 may be similarly selected on a patient by patient basis or using a predetermined value or a value based on a baseline. In general, in order to capture respiration with stimulation for a subject's given minute ventilation, according to one embodiment, the latest stimulation boundary 150 is selected to occur at a time prior to the generation of an inspiration signal from the dorsal respiratory group. Accordingly, the latest stimulation boundary 150 is typically at time substantially before the expected onset of the next breath, i.e., before the end of the rest period. In particular, according to one variation, the latest stimulation boundary 150 is at about 0.9 of the total rest cycle length 130. According to another variation, the latest stimulation boundary is a predetermined time prior to the end of the rest cycle 160, more preferably at about 100 to 500 milliseconds prior to the end 160 of the rest cycle 130.

The identification of the inspiration cycle, exhalation cycle rest period, tidal volume and respiratory rate may be accomplished by sensing the respiration waveform, e.g., with a pneumotachometer, movement sensor or using EMG. An example of such determination is described, for example in related U.S. application Ser. No. 10/686,891 incorporated herein by reference. Various methods and devices that may be used to map ideal electrode placement for a desired result or to optimize stimulation to achieve such result are described in related U.S. Application entitled "SYSTEM AND METHOD FOR MAPPING DIAPHRAGM ELECTRODE SITES" filed on even date herewith and incorporated herein by reference.

FIG. 2 is a flow chart illustrating a baseline determination in accordance with the invention. The device identifies the phase in which stimulation may be applied by sensing the respiratory phase length. This may be used during patient set up to establish patient baseline breathing. The baseline may be determined for several tidal volume levels or for one patient tidal volume, typically in a resting state. Baselines are established on a patient to patient basis because, e.g., each patient may have unique chest/lung compliance that could affect exhalation characteristics.

In step 210, a patient is connected to a flow sensor (e.g., a pneumotachometer).

In step 220 a patient is instructed to breathe at a resting respiratory rate and tidal volume. The respiration waveform is used as a baseline. From the respiration waveform, respiration parameters are measured, e.g., tidal volume, inspiration duration, exhalation duration, rest period, and respiratory rate. Thus the length of each segment of the inspiration cycle is determined for a given tidal volume. The minute ventilation may also be determined from the tidal volume and respiratory rate.

At step 230 which occurs with step 220, the EMG is sensed and the EMG is correlated with the information sensed by the pneumotachometer in step 220. The correlation is useful when the patient is no longer connected to the pneumotachometer. From the EMG and measured tidal volume the tidal volume for a subsequently observed EMG may be estimated or determined. At rest, exhalation is correlated to tidal volume. As tidal volume increases, so does the duration of exhalation. Thus, the exhalation phase for a given title volume can be generally determined as the exhalation phase is generally the same for a given tidal volume.

In step 240 which occurs with steps 220 and 230, diaphragm motion is sensed with a motion sensor. Diaphragm motion indicates when the lungs are inspiring, exhaling or at rest. This step is optional but provides additional correlation information. The motion sensor information is also correlated with EMG and pneumotachometer information.

At step 250 the respiration parameters are stored, i.e. the measured tidal volume and other sensed measured or calculated parameter, and correlated EMG, pneumotachometer and motion sensor data.

At step 260, steps 220 through 250 are repeated for a decreased tidal volume. A patient may be coached or instructed by a provider or programmer via telemetry to breathe at a lower tidal volume and the same measurements are then made as were made for a resting tidal volume.

At step 270, steps 220 through 250 are repeated for an increased tidal volume. A patient may be coached or instructed by a provider or programmer to breathe at a higher tidal volume and the same measurements are then made as were made for a resting tidal volume.

Once the initial baseline data and waveforms are stored, the implanted device may be programmed accordingly and the device turned on.

FIG. 3 illustrates the identification of phase boundaries when the device is in operation.

As illustrated in step 310, the device senses EMG.

In step 320 the EMG is stored along with respiratory parameters that may be ascertained from EMG. This includes the inspiration period where EMG is active, the exhalation and rest period combined where EMG is inactive.

At step 330 if a motion sensor is in use on the diaphragm, then at step 340 the motion detector is used to differentiate between the exhalation phase in which there is diaphragm movement and the rest phase in which there is minimal diaphragm movement.

At step 330, if the motion sensor is not in use on the diaphragm, then at step 350, the data points stored in step 230 of FIG. 2 are used to extrapolate the tidal volume for a given EMG. For a given tidal volume, the exhalation period is generally known, thus the rest period may be determined by subtracting the exhalation period from the combined sensed exhalation and rest periods.

At step 360, following either step 340 or step 350, the stimulation delivery boundaries are determined, i.e. the earliest stimulation boundary 140 and latest stimulation boundary 150 are determined. The stimulation may occur in the same cycle as the EMG or in a subsequent cycle assuming the previous cycle would be approximately the same. In one example, the earliest stimulation boundary is at a predetermined time after the end of the exhalation period. The latest stimulation boundary is a predetermined time before the end of the rest period. In another example the earliest stimulation boundary is after a predetermined fraction of the expected rest cycle has passed. And, the latest stimulation boundary is before a predetermined fraction of the expected rest cycle has passed. Other ways of determining the stimulation phase may be used in accordance with the invention, including but not limited to using optimization as described above with reference to FIG. 1.

At step 370, if treatment is desirable, then at step 380, stimulation is provided during the stimulation phase as programmed. Subsequently, or if no treatment is required, the system resumes monitoring EMG.

According to one aspect of the invention, stimulation is provided that inhibits central respiratory drive for a sufficient duration so that therapeutic stimulation and breathing control may be applied. The therapeutic stimulation breathing is configured to provide a therapeutic benefit at the same time that it acts to inhibit central respiratory drive. According to one aspect the stimulation intensity, duration and respiratory rate are manipulated to inhibit respiratory drive while providing desired stimulation to the diaphragm. For example, at a given respiratory rate and tidal volume during diaphragm stimulation, extending the inspiration or expiration duration (among other things, by increasing stimulation duration and decreasing intensity) effectively shortens the resting period compared to spontaneous breathing and decreases the likelihood of a spontaneous breath between stimulations.

One factor in inhibiting respiratory drive is to stimulate an inspiration between the rest phase boundaries and thereby activate the mechanoreceptors such as the stretch receptors and the proprioreceptors to provide feed back that an individual is actively inspiring. The stretch receptors activate when the airways/lungs stretch and the proprioreceptors activate when respiratory muscles of the diaphragm and/or chest wall contract. Typically output from the respiratory center conducted by efferent nerves to the respiratory muscles are temporarily inhibited by the mechanoreceptor signals until the individual has exhaled.

Another factor that affects respiratory drive is the blood oxygen concentration levels and the partial pressure of carbon dioxide in the blood. A decrease in carbon dioxide levels tends to create a decrease in respiratory drive whereas a decrease in oxygen saturation levels may increase respiratory drive. These levels and thus the chemoreceptors and respiratory drive may be influenced by controlling minute ventilation as is described in related U.S. patent application entitled "System and Method For Diaphragm Stimulation" filed on even date herewith and incorporated herein by reference. Accordingly, parameters that effect minute ventilation e.g., tidal volume and respiratory rate, may be manipulated to control respiratory drive.

FIGS. 4A-4B and 4D illustrate various stimulation schemes in accordance with the invention, for controlling breathing while maintaining central respiratory drive inhibition. FIG. 4C illustrates spontaneous breathing 450 with the dotted line showing what spontaneous breathing would continue to look like without stimulated breathing.

According to one aspect stimulation is provided within the defined stimulation phase (See FIGS. 1 and 3) of the rest phase before the effect of the lack of mechanoreceptor activation allows the brain to initiate inspiration. In addition, tidal volume is maintained which is believed to help prevent other brain receptor functions from causing the initiation of inspiration.

As noted previously, in setting up and programming the device for a specific patient, various stimulation responses may be tested until a desired response (e.g., tidal volume an respiratory rate) is obtained.

Referring to FIG. 4A a set of a series of stimulation pulses 410, 411, 412 is illustrated following a spontaneous breath 400. Each of the series of pulses 410, 411, 412 elicit a slower rate and more shallow breathing (e.g., flow) response 420, 421, 422 in comparison to the spontaneous breaths 490, 496, 497, 498, while each maintaining a tidal volume approximately the same as the tidal volume of the spontaneous breaths 496, 497, 498 (FIG. 4C). Each of the initiation points 402, 404, 406 fall within a stimulation phase that is a less than or is a fraction of the spontaneous breath rest phase 495 (FIG. 4C). The rest phases 403, 405, 407 are shorter. Accordingly, spontaneous breathing is inhibited.

Similarly in FIG. 4B a set of a series of stimulation pulses 440, 441, 442 is illustrated following a spontaneous breath 430. Each of the series of pulses 440, 441, 442 elicit a slower rate and more shallow breathing response 450, 451, 452 in comparison to the spontaneous breaths 490, 496, 497, 498, while each maintaining a tidal volume approximately the same as the tidal volume of the spontaneous breaths 496, 497, 498 (FIG. 4C). Each of the initiation points 432, 434, 436 fall within a stimulation phase that is a less than or is a fraction of the spontaneous breath rest phase 495 (FIG. 4C). The rest phases 433, 435, 437 are shorter than the rest phase 495 while somewhat longer than the rest phases 403, 405, and 407 of FIG. 4A. Accordingly, spontaneous breathing is inhibited.

FIG. 4D illustrates a set of a series of stimulation pulses 470, 471, 472 is illustrated following a spontaneous breath 460. Each of the series of pulses 470, 471, 472 elicit a similar breathing response 480, 481, 482 in comparison to the spontaneous breaths 490, 496, 497, 498, (except the rate is faster) thus each maintaining a tidal volume approximately the same as the tidal volume of the spontaneous breaths 490, 496, 497, 498. Each of the initiation points 462, 464, 466 fall within a stimulation phase that is a less than or is a fraction of the spontaneous breath rest phase 495 (FIG. 4C). While the breathing responses 480, 481, 482 are similar or the same as those of the spontaneous breaths, 496, 497, 498, the respiration rate is increased. Accordingly, spontaneous breathing is inhibited.

The stimulation scheme of the invention may be used in a number of applications. In general, a patient's breathing is captured by the stimulator and breathing stimulation is applied to control breathing for a period of time.

In one application, breathing is stimulated to increase oxygen saturation levels for a period of time. It is believed that this scheme will allow positive remodeling of the heart by reducing the load on the heart for a period of time, e.g., for one or more time intervals during sleep. Reduced contractility and cardiac output for a period of time provides an opportunity for an overloaded heart to rest. The oxygen saturation levels can be increased by increasing minute ventilation. Therefore one aspect of the invention is a device and method for treating heart failure patients by providing breathing stimulation for periods of time that increase oxygen saturation levels.

Examples of a breathing therapy schemes are shown in FIGS. 5-8. As shown in FIG. 5, during normal breathing tidal volume respiratory rate and minute ventilation are observed as described with respect to FIGS. 1-3 herein. Tidal volume is maintained at the normal level while respiratory rate is increased, thus increasing minute ventilation and SaO2 levels, decreasing PCO2 levels, and therefore maintaining central respiratory drive inhibition. This therapy mode is maintained for a programmable amount of time, e.g., for one or more intervals of time during the night or during the day. After the breathing therapy mode, breathing is normalized to allow PCO2 to slowly increase so spontaneous breathing can be restored. This may be accomplished by returning respiratory rate back to normal and maintaining normal tidal volume to increase PCO2 and thereby encourage the return of intrinsic breathing and respiratory drive. If after the stimulator stimulates breathing at a normal rate for a period of time and spontaneous breathing has not returned, the patient is weaned from the stimulator by further decreasing the respiratory rate and therefore minute ventilation. This will allow intrinsic breathing and respiratory drive to return by allowing an increase in PCO2.

FIG. 6 is a flow chart illustrating the scheme set forth in FIG. 5. At step 610 the breathing therapy scheme is activated, e.g. at a programmed time.

At step 620, control of breathing is taken over either immediately as described with respect to FIG. 7, or gradually as described with respect to FIG. 8.

At step 630 the stimulation delivery boundaries identified as described in FIG. 2 are recalled (which have been dynamically observed and recorded).

At step 640 the diaphragm is stimulated at an increased minute ventilation for a given or programmed duration.

At step 650 breathing stimulation is normalized and the normalization mode is activated. Stimulation at a normal minute ventilation is provided for a given duration or until spontaneous breathing returns.

At step 660, the weaning mode is activated and minute ventilation is decreased for a given duration or until spontaneous breathing returns.

Referring to FIG. 7, immediate control begins after a period of normal breathing 700 by taking over breathing at a point 705 within an identified stimulation phase. Stimulation of breathing at the increased respiratory rate is continuously applied for the breathing therapy portion 710. Stimulation is then normalized for a period of normalization 720 and the patient is weaned for a period of weaning 730. While not specifically shown in FIG. 7, stimulation continues until the return of spontaneous breathing.

FIG. 8 illustrates a gradual control mode. In the first portion 810 of the gradual control mode stimulated breaths 801 are induced between spontaneous breaths 800. The effective minute ventilation is gradually increased as the rest period 812 between the spontaneous breath 800 and the subsequent stimulated breath 801 are shorter than the intrinsic rest period 811. Over time in this first portion 810 of the gradual mode, SaO2 will increase and PCO2 will decrease gradually decreasing the respiratory drive. The length of the rest period is determined, e.g., using a motion sensor, until it reaches a critical length that has increased due to decreased respiratory drive (e.g. at rest period 820 ending at 802). At that point breathing is controlled by the stimulator as it has transitioned to the immediate control mode for a period of time 830. Then breathing is normalized 840 and finally the patient is weaned 850.

Another aspect of the invention provides for breathing therapy in treating apnea. It is believed that stimulated breathing prior to or during apnea may stabilize the broad swings of blood gas concentrations that occur during cycles of Cheyne-Stokes and apnea. Further it is believed that diaphragmatic stimulation during apnea may stimulate vagal afferent signals to the respiratory center and thus may maintain vagal tone associated with restful sleeping. Vagal tone has a calming effect on heart rate, blood pressure and cardiac output during restful sleep stages. Furthermore, diaphragmatic stimulation may prevent a fall in oxygen saturation that would typically initiate an arousal episode during apnea. Arousal episodes are associated with increases of sympathetic nerve activity which increases ventilation rate, heart rate and blood pressure. If oxygen saturation falls below a threshold, it is believed that hyperventilation will attempt to compensate for the falling oxygen saturation and also create arousal. Accordingly the invention provides a device and method for preventing apnea arousals. The invention also provides a device and method for providing greater periods of restful sleep particularly in patients suffering from ongoing bouts of apnea and resulting arousal from sleep.

Referring to FIG. 9 at step 910 apnea is detected and an episode is initiated. Apnea may be detected e.g., by a lack of EMG for a given period of time.

At step 920, stimulation is provided. If stimulation is provided during an apnea interval, (preferably at the beginning of the apnea level before SaO2 levels are depleted) stimulation is provided at a predetermined rate and tidal volume based on previous baseline determinations. In particular stimulation is provided at lower minute ventilation than normal. This is to gradually allow for more oxygenation than will occur during apnea while also allowing an increase in the PCO2 levels until the respiratory drive increases at least above the apneac threshold, and spontaneous breathing at a desired level returns. Cheyne-Stokes and apnea tend to occur in repeated cycles in heart failure patients. This is believed to occur in part due to the delay in the feedback or chemoreceptor sensing due to circulatory delay which is common in heart failure patients. The purpose of the apnea therapy described herein is to stabilize the blood gas levels more gradually and to reduce the extreme fluctuations between Cheyne-Stokes hyperventilation and apnea.

At step 930, the stimulation rate is set and may gradually be reduced by increasing the intervals between successive breaths or stimulations. If no EMG 940 is sensed within interval 930 or a sensed EMG does not meet the amplitude criterion and the interval length has not reached a maximum length, then the stimulation is delivered at step 920 and the cycle 930 & 940 repeated. If an EMG is sensed 940 within the 930 interval and meets amplitude criterion then the stimulation will be inhibited at step 950. If a defined number of successive sensed EMGs meeting step 940 criterion are not met then the interval is again set at step 930. If a defined number of successive sensed EMGs meeting step 940 criterion are met in step 960 then the episode is over and the device returns to apnea detection mode 910.

FIG. 10 illustrates apnea treatment as described with respect to FIG. 9. The waveform at 1000 may be a normal intrinsic breath. At 1010 a breath with an increased amplitude may be a precursor to Cheyne-Stokes hyperventilation that may indicate the imminent onset of Cheyne-Stokes. At 1020 Cheyne-Stokes hyperventilation is at a peak amplitude. At 1030 the amplitude is decreasing indication the imminent onset of apnea. At 1040, apnea has occurred. At 1010, 1020, or 1030, a precursor to apnea may be sensed and stimulation may be provided to take over breathing in a manner similar to that described with reference to FIGS. 5-8. The stimulation may be adjusted to increase or decrease minute ventilation to stabilize blood gas fluctuations and avoid further episodes of Cheyne-Stokes and/or apnea. Maintaining stable blood gas levels with stimulation may prevent Cheyne-Stokes hyperventilation and hence avoid arousal events otherwise associated with large swings of these gases.

If detection of apnea occurs, e.g., at point 1040, then stimulation begins at 1050. As described with respect to FIG. 9, stimulation is at minute ventilation that is reduced from a normal baseline. At 1060 the intervals between stimulation cycles increase. At 1070 an EMG is sensed but it is not at a desired level and the stimulation continues. At 1080 an EMG is sensed and stimulation is inhibited until an interval passes. At 1090 a set interval has passed without spontaneous breathing and stimulation then resumes. At 1095 spontaneous breathing has resumed and continues for a requisite number of cycles (until point 1099 is reached). It is then determined that the episode is over and the system returns to apnea sensing mode.

As an alternative to detecting apnea as an episode is occurring, precursors to apnea or to Cheyne-Stokes may be sensed and treated. A precursor to apnea may be detected in a number of ways, for example, by detecting Cheyne-Stokes hyperventilation or a precursor to Cheyne-Stokes hyperventilation. Also a precursor to apnea may be detected by detecting periodic breathing throughout a day prior to night time. If this is the case stimulation is delivered throughout the night, in intervals as described with respect to FIGS. 5-8. In addition, the device may be set to detect actual apnea events if they occur in spite of administering breathing therapy as described with respect to FIGS. 9 and 10 herein. Detection of precursors is described in more detail in related U.S. Application entitled: "BREATHING DISORDER AND PRECURSOR PREDICTOR AND THERAPY DELIVERY DEVICE AND METHOD" filed on even date herewith and incorporated herein by reference.

In accordance with another aspect of the invention, provides for treatment of hypertension. Studies have shown that patients coached to breath at about 6 breaths per minute have a reduction in blood pressure and resting oxygen saturation is improved.

FIGS. 11A-B illustrate an example of a hypertension breathing therapy device. According to the example, capture of breathing as described in FIGS. 5-8 may occur on a nightly basis for specific preprogrammed durations. In addition stimulation may also be provided during an exhalation cycle to further extend the length of the active breathing portion (inspiration and exhalation) of the respiration cycle. The duration of the rest period is greatly reduced so that the central respiratory drive may remain inhibited. The minute ventilation is maintained in accordance with a baseline determined as described with reference to FIG. 2. The goal is to create long slow breathing, e.g., at about 6 cycles per minute or at another rate that provides desired therapy.

FIGS. 11A-B illustrates an example of inducing slow controlled breathing therapy. FIG. 11A illustrates the breathing morphology while FIG. 11B illustrates the corresponding stimulation bursts or series of pulses. During the first period 1100 spontaneous breathing is occurring which can be used as a baseline. During a second period 1110, breathing is captured and the breathing rate is slowed. During period 1110, stimulation induces an inspiration cycle with a passive exhalation and a rest period as in spontaneous breathing.

Subsequently during period 1120 stimulation ramps up to induce an inspiration cycle, as in period 1110, and gradually ramps down during exhalation to extend the length of the exhalation cycle. Thus, the normally passive exhalation phase is now influenced with active stimulation. The increase in the duration of the active breathing portion of the respiration cycle decreases the rest phase duration which tends to inhibit the occurrence of spontaneous breathing. During period 1120 minute ventilation is approximately equal to minute ventilation during period 1110 which is achieved by increasing the tidal volume and decreasing the rate. In the period 1120 (the therapy cycle), the stimulation 1131 becomes longer in duration than stimulation 1130, further extending the duration of the breaths and decreasing the rest phase, which inhibits spontaneous breathing and maintains a decreased respiration rate. Then the stimulation 1132 decreases in duration and stimulation is inhibited. After breathing therapy is complete, the stimulation is turned off or stimulation is gradually returned to normal breathing in a manner similar to that described in examples above. Spontaneous breathing will then resume. In accordance with this aspect of the invention preferably the breathing rate is reduced to 20 breaths per minute or less, more preferably about 10 breaths per minute or less and most preferably between about 4 and 8 breaths per minute.

The respiratory drive inhibition may also be used in treating COPD patients. COPD patients have difficulties exhaling $CO_2$ and therefore typically retain high levels of $CO_2$ in their blood. Low levels of inspiration with high levels of exhalation may be induced by inducing longer periods of exhalation in a manner similar to that described with respect to FIGS. 11A-11B where the exhalation period is extended.

While the invention has been described in detail with reference to preferred embodiments thereof, it will be apparent to one skilled in the art that various changes can be made, and equivalents employed, without departing from the scope of the invention.

What is claimed is:

1. A method for treating a breathing disorder in a patient breathing, intrinsically comprising:
   providing a device comprising a control unit, a sensor and a signal generator, wherein said control unit receives information from said sensor and is programmed to cause said signal generator to generate an electrically stimulating signal to diaphragm and/or phrenic nerve tissue;
   identifying the phases within an intrinsic breathing cycle of a patient, said phases comprising the inspiration, exhalation, and rest periods of the intrinsic breathing cycle of the patient utilizing said sensor;
   delivering the electrically stimulating signal during the rest period of the intrinsic respiratory cycle of said patient; and,
   electrically stimulating the diaphragm or phrenic nerve tissue of the patient by delivering a burst or series of pulses as the electrically stimulating signal at a time of the rest period prior to the expected onset of the next breath when breathing is present, providing therapeutic stimulation such that diaphragm movement of the patient is controlled to thereby inhibit central respiratory drive to prevent the onset or to reduce frequency of a breathing disorder.

2. The method of claim 1 wherein the step of electrically stimulating further comprises providing electrical stimulation directed to stabilizing swings in levels done Or more blood gas wherein the stabilization of the swings reduces occurrence of a breathing disorder.

3. The method of claim 2 wherein the step of providing electrical stimulation directed to stabilizing swings in levels of one or more blood gas comprises:
   preventing a fall in oxygen saturation to thereby reduce a possibility of an arousal occurring.

4. The method of claim 1 wherein the step of electrically stimulating comprises providing stimulation at a point that is about 90% of the total rest period length.

5. The method of claim 1 wherein the step of stimulating comprises providing stimulation at a point about 100 to 500 milliseconds prior to the end of the rest period.

6. The method of claim 1 further comprising providing a series of sequential stimulations subsequent to providing stimulation during an exhalation period.

7. The method of claim 1 wherein the step of electrically stimulating comprises further providing electrical stimulation to manipulate minute ventilation.

8. The method of claim 1 wherein the step of electrically stimulating comprises farther providing electrical stimulation to manipulate a duration of an exhalation cycle with respect to a duration of an inspiration cycle.

9. The method of claim 1 wherein the step of electrically stimulating comprises stimulating diaphragm and/or phrenic nerve tissue via one or more electrodes in contact with the tissue.

10. The method of claim 9 further comprising providing an implantable unit placed in electrical communication with the tissue.

11. The method of claim 1 wherein the step of identifying the phases within an intrinsic breathing cycle of a patient comprises identifying stimulation boundaries for earliest and latest periods of stimulation within the phase of the intrinsic breathing cycle.

12. The method of claim 11 wherein the earliest period of stimulation comprises a period following exhalation.

13. The method of claim 11 wherein the latest period of stimulation comprises a period prior to onset of a subsequent spontaneous breath.

14. The method of claim 1 further comprising normalizing the electrical stimulation during a period of normalization.

15. The method of claim 14 further comprising weaning the patient from the electrical stimulation until spontaneous breathing by the patient resumes.

* * * * *